United States Patent [19]

Saperston

[11] Patent Number: 5,267,942
[45] Date of Patent: Dec. 7, 1993

[54] METHOD FOR INFLUENCING PHYSIOLOGICAL PROCESSES THROUGH PHYSIOLOGICALLY INTERACTIVE STIMULI

[75] Inventor: Bruce M. Saperston, Logan, Utah

[73] Assignee: Utah State University Foundation, Logan, Utah

[21] Appl. No.: 869,922

[22] Filed: Apr. 20, 1992

[51] Int. Cl.⁵ .......................................... A61M 21/00
[52] U.S. Cl. .................................... 600/28; 128/731; 128/905
[58] Field of Search .................................. 600/26–28; 128/731–732, 905

[56] References Cited

U.S. PATENT DOCUMENTS

| | | | |
|---|---|---|---|
| 4,282,864 | 8/1981 | Pizer | 600/26 |
| 4,883,067 | 11/1989 | Knispel et al. | 600/28 |
| 5,036,858 | 8/1991 | Carter et al. | 600/27 |
| 5,076,281 | 12/1991 | Gavish | 600/28 |

Primary Examiner—Lee S. Cohen
Assistant Examiner—J. P. Lacyk
Attorney, Agent, or Firm—Thorpe, North & Western

[57] ABSTRACT

A method for interactively entraining a patient's heart rate to a target rate or frequency includes the steps of determining the patient's heart rate through a heart rate monitor and exposing the patient to music having a tempo within approximately one (1) beat of the heart rate. The heart rate is again determined, and if it has changed the tempo of the music is likewise changed in order to be within approximately one (1) beat of the heart rate. The process is continued until the target rate is reached. Vibrational bass tones can be added to enhance the entrainment. Similar methods can be used to entrain respiration rate and fundamental brain wave frequencies, in the latter case using continuous tones of music having repetition frequencies within the entrainment range.

34 Claims, 5 Drawing Sheets

METHOD FOR INFLUENCING PHYSIOLOGICAL PROCESSES THROUGH PHYSIOLOGICALLY INTERACTIVE STIMULI

FIELD OF THE INVENTION

The present invention concerns the field of music therapy methods and devices, and particularly those methods and devices adapted to influence physiological processes in order to achieve a desired result, such as stimulation or relaxation of a patient.

BACKGROUND OF THE INVENTION

Music therapy is the scientific application of music or sound for healing, relaxation, fighting depression, and the like, in patients such as the physically and mentally ill, the mentally retarded, and aged. The fact that music affects persons in various ways has long been known, and numerous methods of applying particular types of music or sounds in certain ways to achieve particular results have been disclosed in the art. Many of these methods aim to alter physiological properties such as muscle tension, and rhythms such as brain wave frequency, heart rate, respiration rate, or circadian rhythms, e.g., body temperature variation, hormone level, blood pressure, blood sugar, and concentrations of essential biochemicals in the nervous system.

The traditional method of presenting music to a patient for this purpose comprises choosing a suitable type of music, such as a soothing classical or romantic piece if a relaxation of muscle tension is desired, and presenting it unchanged to the patient. With the development of new technologies such as realistic synthesized sound, computer technology, and convenient and non-obtrusive patient observatory mechanisms, however, new methods of provoking physiological responses to music are possible.

A technique that was developed as a departure from traditional methods of psychological therapy, was the "iso-moodic" principle, which matches musical stimuli to a patient's existing mood and subsequently changes the stimuli in the direction in which the patient's mood is to be influenced. This technique has been found to be applicable to physiological changes as well. Altshuler, A Psychiatrist's Experience with Music as a Therapeutic Agent, in *Music and Medicine*, eds. Schullian et al., Book for Libraries Press (1948); Pignatiello et al., A Psychophysiological Comparison of the Velton and Musical Mood Induction Techniques, 26 *J. of Music Therapy* 140 (1989); Rider, Entrainment Mechanisms are Involved in Pain Reduction, Muscle Relaxation, and Music-Mediated Imagery, 22 *J. of Music Therapy* 183 (1985); Rider et al., The Effect of Music, Imagery, and Relaxation on Adrenal Corticosteroids and the Re-Entrainment of Circadian Rhythms, 22 *J. of Music Therapy* 46 (1985).

An example of the iso-moodic principle affecting physiology is documented by Rider, supra, who described a presentation of iso-moodic music to spinal cord injury patients for reduction of muscle tension or electromyograph activity (EMG). The music shifted in a pre-determined fashion and sequence from unpleasant to pleasant; specifically, from a rhythm of an emotionally challenging accelerating ⅞ meter to a comfortable andante 4/4 meter. Rider found that the iso-moodic music was more effective in reducing muscle tension than four other types of music which were also presented: minimalist, jazz, impressionistic, and music preferred by the patients.

Saperston found that iso-moodic music was more effective than sedative music or silence in reducing EMG activity. Saperston, Music-Based Individualized Relaxation Training (MBIRT): Sequential Stress Reduction Techniques for the Behaviorally Disturbed Mentally Retarded, 6 *Music Therapy Perspectives* 26 (1989). Pignatiello et al., supra, found that iso-moodic music affected systolic blood pressure.

Notwithstanding the above, no one in the prior art has used the iso principle for anything besides a general shift in mood, the physiological responses resulting primarily as a side effect of the patient's changing mood. Iso-type music has not been structured to directly affect a specific ongoing physiological response of the patient. In addition, prior art iso-moodic music stimuli have a fixed structure, sequence, and speed; they d not take into account the reaction of the patient during presentation of the stimuli, which may be neutral or contrary to expectations. Though iso-moodic music which coaxes the patient from the initial state to the desired state through traversing that same path itself has been found to be more effective than traditional music presentation techniques, it is desirable to find even more effective methods.

The concept of the Huygens phenomenon, or entrainment, has proven useful in influencing physiological responses. Entrainment is the locking into phase of previously out-of-step oscillators, such as two pendulum clocks mounted on the same bracket. An oscillator can be anything that vibrates in a regular periodic manner. "Whenever two or more oscillators in the same field are pulsing at nearly the same time, they tend to lock in so that they are pulsing at exactly the same time. The reason, simply stated, is that nature seeks the most efficient energy state, and it takes less energy to pulse in cooperation than in opposition." Leonard, *The Silent Pulse*, Elsevier-Dutton Publ. Co. p. 12 (1978). It is important to note that the two oscillators must be pulsing at nearly the same time in order for entrainment to occur.

Various physiological studies have dealt with entrainment, largely with regard to circadian rhythms, and have found that physiological process rhythms are entrained to each other (internal synchronization), with environmental time cues (external synchronization), or both. It has been found that the desynchronization of physiological processes which are normally entrained can have deleterious effects on physical health, mental health, task performance, and behavior both in normal patients and those with existing physical or mental disorders.

Rider and his co-workers, supra, have found that desynchronized corticosteriod and body temperature circadian rhythms can be re-entrained through a general treatment comprising music, progressive muscle relaxation, and imagery.

More specifically, other researchers have found that auditory or musical stimuli can be systematically presented as synchronizers to influence predictable changes in physiological responses through entrainment. One study found that respiration rates approximated the rates of a regularly recurring tone. Lovell et al., Physiological and Motor Responses to a Regularly Recurring Sound: A Study in Monotony, 30 *J. of Experimental Psychology* 435 (1942). Another demonstrated that respiratory patterns could be entrained by prerecorded rhythmic music. Haas et al., Effects of Perceived Musical Rhythm on Respiratory Pattern, 62(3) *J. of Applied Physiology* 1185 (1986). Another reported that heart rates were entrained through the presentation of audible clicks at a precise time in the cardiac cycle measured from each R-wave of the subjects' electrocardiograms. Bason et al., Control of the Heart Rate by External Stimuli, 238(5362) *Nature* 279 (1972).

Other prior art of interest includes Landstrom et al., Changes in Wakefulness During Exposure to Whole Body Vibration. 61 *Electroencephalography and Clinical Neurophysiology* 411 (1985), in which a regular tone of 3 Hz presented to a patient tended to shift the patient's electroencephalogram from the alpha frequency band to the theta frequency band.

In addition to the above techniques, drug and biofeedback treatments currently are used to influence therapeutic changes in physiological processes. However, some drugs have deleterious effects, and many individuals with cognitive defects, e.g., mental retardation and dementia, those persons with emotional problems, and young children cannot benefit from traditional biofeedback training.

OBJECTS AND SUMMARY OF THE INVENTION

It is therefore an object of the present invention to improve on prior art methods of influencing physiological processes.

It is a further object of the invention to systematically manipulate music presented to a patient in relation to ongoing physiological responses in order to effectively influence such responses.

It is a further object of the invention to change a patient's heart rate or EEG frequency band through interactive musical stimuli.

It is a further object of the invention to couple interactive musical stimuli with interactive tactile stimuli to carry out the above objects.

According to a first aspect of the invention, a method of interactively entraining a physiological process having a determinable frequency in a patient toward a target frequency comprises the steps of making a first determination of the frequency of the physiological process, presenting sound stimuli to the patient during a predetermined first time interval, the sound stimuli having a frequency within a predetermined entrainment range of the frequency of the physiological process, and making a second determination of the frequency of the physiological process, thereby determining the direction of and extent to which the physiological process frequency has varied from the time of the first determination. The frequency of the sound stimuli is then changed to approximately the same extent and in the same direction as the change in frequency of the physiological process, and the sound stimuli is presented to the patient during a predetermined second time interval. In a preferred embodiment, the steps are repeated until the frequency of the physiological process is approximately the same as the target frequency, at which time the frequency of the sound stimuli is made approximately the same as the target frequency and the frequency of the physiological process is monitored and the frequency of the sound stimuli is changed to remain within the entrainment range of the physiological process frequency if the latter substantially deviates from the target frequency.

According to a second aspect of the invention, a method of influencing the rate of organismic rhythms comprises the steps of determining the frequency of the organismic rhythm at a first point in time, exposing the organism to external rhythmic stimuli having a frequency near to but not identical to the frequency of the organismic rhythm determined at the first point in time, determining the frequency of the organismic rhythm at a second point in time, and exposing the organism to external rhythmic stimuli having a frequency near to but not identical to the frequency of the organismic rhythm determined at the second point in time.

In accordance with a third aspect of the invention, a method of varying a person's heart rate from a first frequency to a second frequency comprises the steps of (1) exposing the person to music having a tempo within an entrainment range of the heart rate at the first frequency, (2) ascertaining the change, if any, in the person's heart rate, (3) determining whether the music tempo has fallen outside the entrainment range of the heart rate and if so, changing the tempo to fall once again within the entrainment range of the heart rate, (4) exposing the person to the music with the changed tempo, and (5) repeating steps (1) through (4) until the heart rate reaches the second frequency. In a preferred embodiment, the person may also be exposed to low frequency tones corresponding to the bass part of the music, and/or tactile stimulation corresponding to the tempo of the music.

In accordance with a fourth aspect of the invention, a method of changing a component brain wave frequency of a person from a first frequency to a target frequency comprises the steps of (1) determining the first frequency of the component frequency at a first point in time, (2) subjecting the person to a first sound tone having a frequency near the first frequency, (3) determining the frequency of the component frequency at a second point in time, (4) subjecting the person to a second sound tone, instead of the first sound tone, having a frequency near the frequency of the component frequency as determined at the second point in time, and (5) repeating steps (1) through (4) until the component frequency approximates the target frequency. In preferred embodiments, the sound tone frequencies comprise either repetition frequencies or beat frequencies.

BRIEF DESCRIPTION OF THE DRAWINGS

These and other objects, aspects, and embodiments of the present invention are described herein with regard to the following drawing figures, of which.

DETAILED DESCRIPTION OF THE INVENTION

Figure 1:
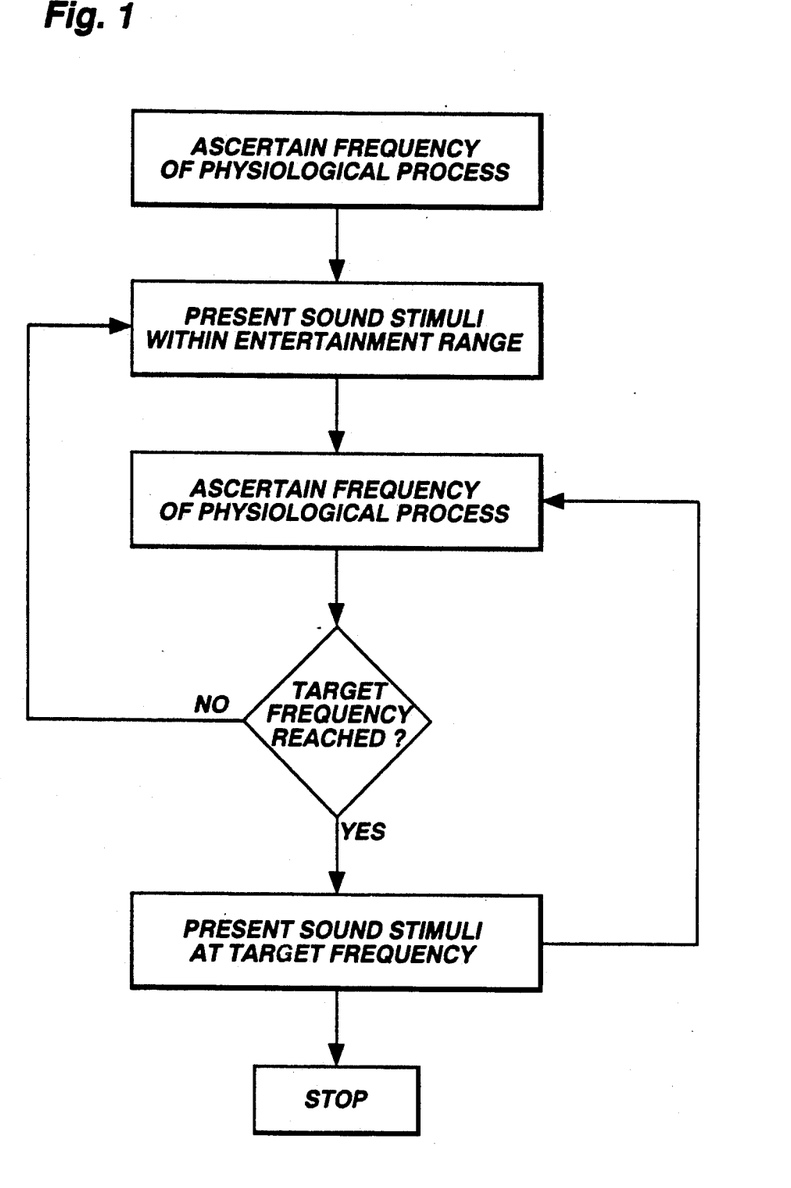
FIG. 1 is a flow chart of an example of a method of interactively entraining physiological rhythms according to the invention.

Referring first to FIG. 1, a method of interactively entraining a physiological rhythm according to the invention is illustrated in flow chart form. The frequency of the physiological process sought to be entrained, influenced, or changed first is ascertained. This is a rhythm in a patient such as heart rate, brain wave frequency, respiration rate, and the like. After the frequency of the physiological process is determined, sound stimuli is presented to the patient, the sound stimuli having a frequency within the entrainment range of the physiological process, which can be determined through routine experimentation, which will be apparent to those skilled in the art in light of this disclosure.

Entrainment ranges, meaning the range in which the frequency of the sound stimuli may vary from the frequency of the physiological process while still entraining the physiological process, may vary widely depending on the particular patient and the physiological process sought to be changed. It should be noted that, generally, the sound stimuli will be most effective in entraining the physiological process if its frequency is as close as possible to the frequency of the physiological process. The entrainment range in most cases is believed to lack an exact cutoff frequency; rather, the sound stimuli gradually diminishes in entrainment effectiveness as its frequency diverges from that of the physiological process. Practitioners can set their own cutoff frequencies for the entrainment range used with the invention based on how quickly the physiological process is sought to be entrained and the technological limitations of available equipment.

If the target frequency, i.e., the frequency to which the practitioner hopes to change the physiological frequency, is slower than the initially-determined physiological frequency, the frequency of the sound stimuli will be set slightly slower than the physiological frequency in order to entrain the latter in that direction. The reverse will apply if the target frequency is faster than the initially-determined physiological frequency.

After a predetermined testing time interval has passed, such as one (1) second, during which the sound stimuli is presented to the patient, the frequency of the physiological process is again ascertained. If the physiological process frequency has reached the target frequency, the sound stimuli is then presented at a frequency approximately equal to the frequency of the physiological process in order to maintain the physiological process at the target frequency. The physiological frequency continues to be ascertained after successive testing time intervals; if it strays from the target frequency, the sound stimuli frequency is changed as needed to fall within the entrainment range to bring the physiological frequency back to the target frequency. This continues until the treatment session is completed. Of course, a practitioner may choose to end the treatment as soon as the target frequency is reached if desired. Treatment steps other than that above-described can be used as needed once the target frequency is reached, depending on the needs of the particular patient and the aims of the treatment session.

If the physiological frequency has not reached the target frequency, the sound stimuli is again presented within the entrainment rang of the physiological frequency to coax it to the target frequency. If the physiological frequency has not changed during the testing time interval, the sound stimuli frequency may remain unchanged, since it is already within the entrainment range, or it may be altered to bring it closer to or farther from the physiological frequency in an attempt to initiate entrainment. If the physiological frequency has changed, the sound stimuli frequency may remain unchanged if it is still within the entrainment range of the physiological frequency, or it may be changed to bring it into the physiological frequency entrainment range if it has moved outside of it. It is anticipated that in most cases the sound stimuli will be changed to a degree similar to the degree to which the physiological frequency has changed to keep the frequency difference between the two relatively constant.

Ideally, the physiological frequency will continually move toward the target frequency through the entrainment of the sound stimuli, but as a practical matter the physiological frequency often changes in the opposite direction. In either case, the sound stimuli frequency is changed to remain within the entrainment range such that it continues to coax the physiological frequency toward the target frequency no matter how it might momentarily change. This is a great advantage over the prior art, since a fixed sound stimuli frequency cannot move to remain within the entrainment range when the physiological frequency changes contrary to expectations, and thus it will cease to have any entrainment effect on the physiological frequency unless and until the latter moves within the entrainment range of its own accord.

The shorter the testing time interval, the more effective the interactive method will be, since with shorter intervals the frequency of the sound stimuli will be changed more often to stay within the entrainment range and thus stay within the range a greater percentage of time. Depending on the circumstances, the testing time interval can be as short as testing conditions and technologies allow, or it can be lengthened to very long periods of time for physiological processes which do not change quickly.

Figure 2:
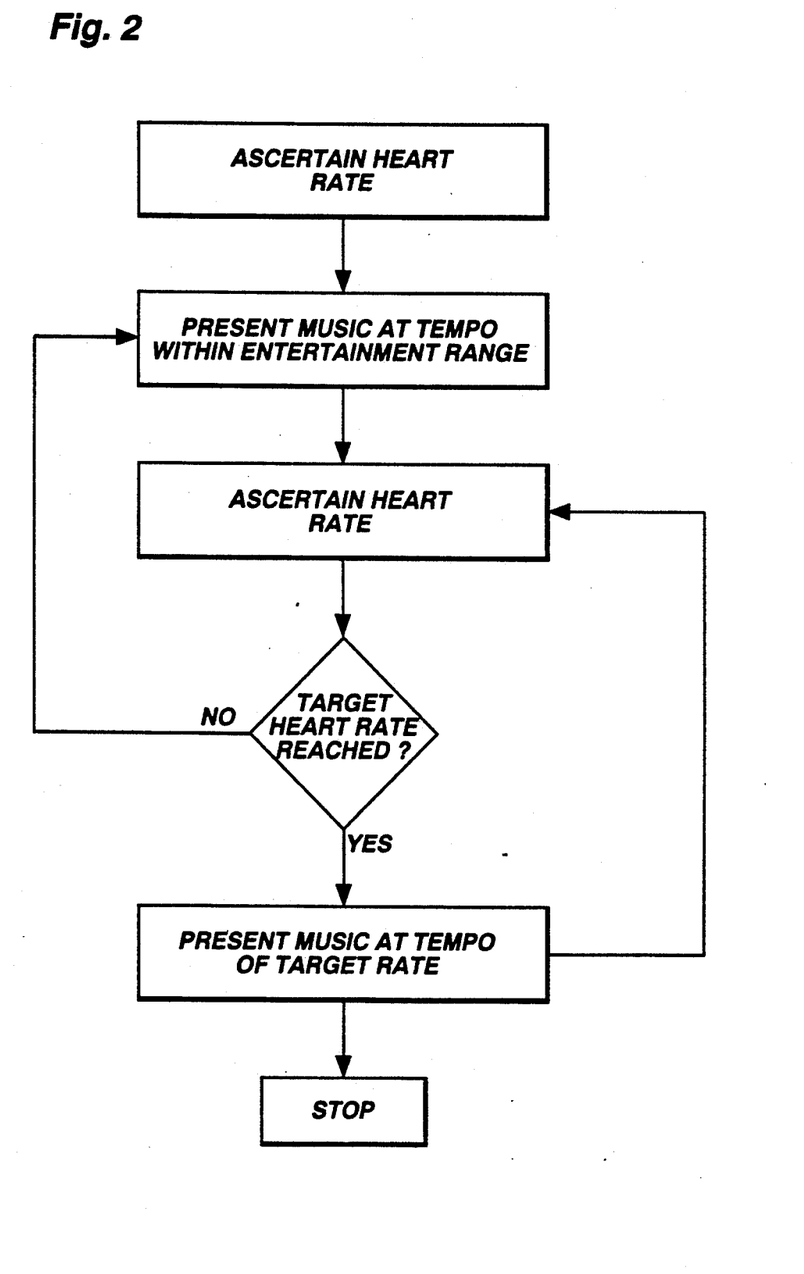
FIG. 2 is a flow chart of an example of a method of interactively entraining heart rate according to the invention.

Referring now to FIG. 2, a method of interactive entrainment according to the invention is shown which is adapted to entrain heart rate frequency. In this case, the heart rate of the patient is ascertained, and music is presented to the patient, the music having a tempo at a frequency within the entrainment range. "Tempo" is used herein with its conventional meaning. Nevertheless, it can also be used to mean the frequency of any beat or pulsation generated by the music.

After the testing time interval, the heart rate of the patient is again ascertained and tested to see if it has reached the target state, and the tempo of the music is changed as needed as described in connection with FIG. 1.

Modern technology has made it possible to change the tempo of synthesizer music while keeping all other elements of the music constant. This has been advantageously used with regard to the method of FIG. 2. A particular treatment study using the method of FIG. 2 is described infra in the example located at the end of this disclosure.

The method of FIG. 2, as well as all other methods and embodiments of the invention, may be done either manually or automatically. Specifically to FIG. 2, a computer may be used to read output data from a heart rate monitor and present preprogrammed synthesizer music at tempi within the entrainment range of the ongoing heart rate. Appropriate software would enable the practitioner to set the relationship between the tempo and the heart rate within an entrainment range of one (1) beat to one one-hundredth (0.01) of a beat per minute.

The method of FIG. 2 may be used to influence physiological rhythms other than heart rate, e.g., respiration rate. Other physiological applications will be apparent to those skilled in the art.

Altering heart rate as herein contemplated has practical applications including controlling heart rate during medical and surgical procedures instead of drugs, controlling heart rates of premature and at-risk infants in neo-natal centers or in the home, assisting patients with hypertension or other cardiac problems in maintaining therapeutic heart rates, and providing stress-reduction techniques to those who cannot or will not benefit from biofeedback training such as mentally retarded persons, the severely emotionally disturbed, and young children.

Figure 3:
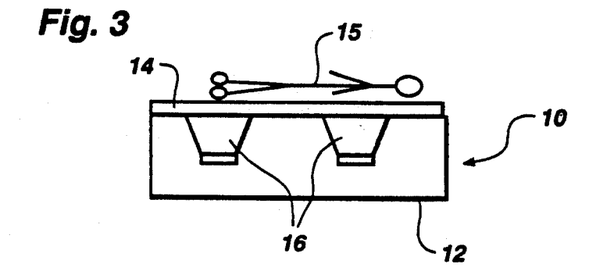
FIG. 3 is a side view in cross section of an example of a bed used to impart vibrational stimuli to a patient.
Figure 4:
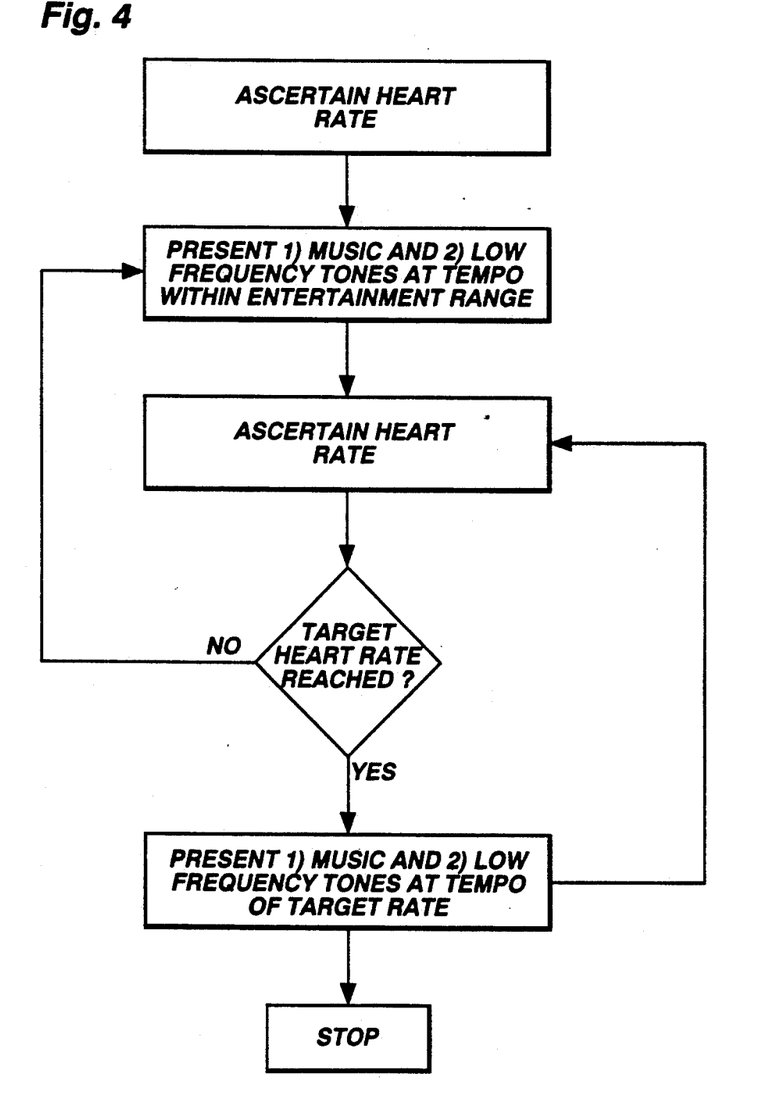
FIG. 4 is a flow chart of another example of a method of interactively entraining heart rate according to the invention.

Referring now to FIG. 3, an example of a bed 10 for the use of low-frequency tones in another embodiment of the invention, described with reference to FIG. 4, is shown. The bed 10 comprises a frame 12 over which a thin foam mattress 14 is placed on which the patient 15 lies. Large speakers 16, e.g., 12-inch subwoofers, flat +/−3dB at 30 Hz, are placed upright in the bed. The bed is commercially available, or may be built by the practitioner.

Referring now to FIG. 4, another embodiment of a method according to the invention is shown in flow chart form. This method is similar to the method described with reference to FIG. 2, but in addition to presenting music at a tempo within the entrainment range of the heart rate, the bed 10 shown in FIG. 3 is also used to present low frequency tones, i.e., 20 to 80 Hz, as the bass part of the music. A strong amplifier (not shown), e.g., 100 watts per channel (though other levels of amplification will also be suitable), is used to amplify the tones and feed them to the speakers 16 such that the patient 16 both hears the tones and feels them as vibrational stimuli within the body. These low frequency tones add an additional dimension to the method of FIG. 2, shown in FIG. 4, of tactile or physical interactive entrainment stimulation in addition to auditory stimulation, and the tones enhance the effectiveness of the entrainment in many cases.

The low frequency interactive entrainment tones can be used alone, i.e., without music, if desired, though it is believed that the combination with music is more effective since appropriate music can be chosen to enhance the entrainment effect, e.g., soothing music for entrainment to a lower heart rate, exciting music for entrainment to a higher heart rate.

As with regard to the method of FIG. 2, the method of FIG. 4 can also be used for interactive entrainment of other appropriate physiological processes.

Figure 5:
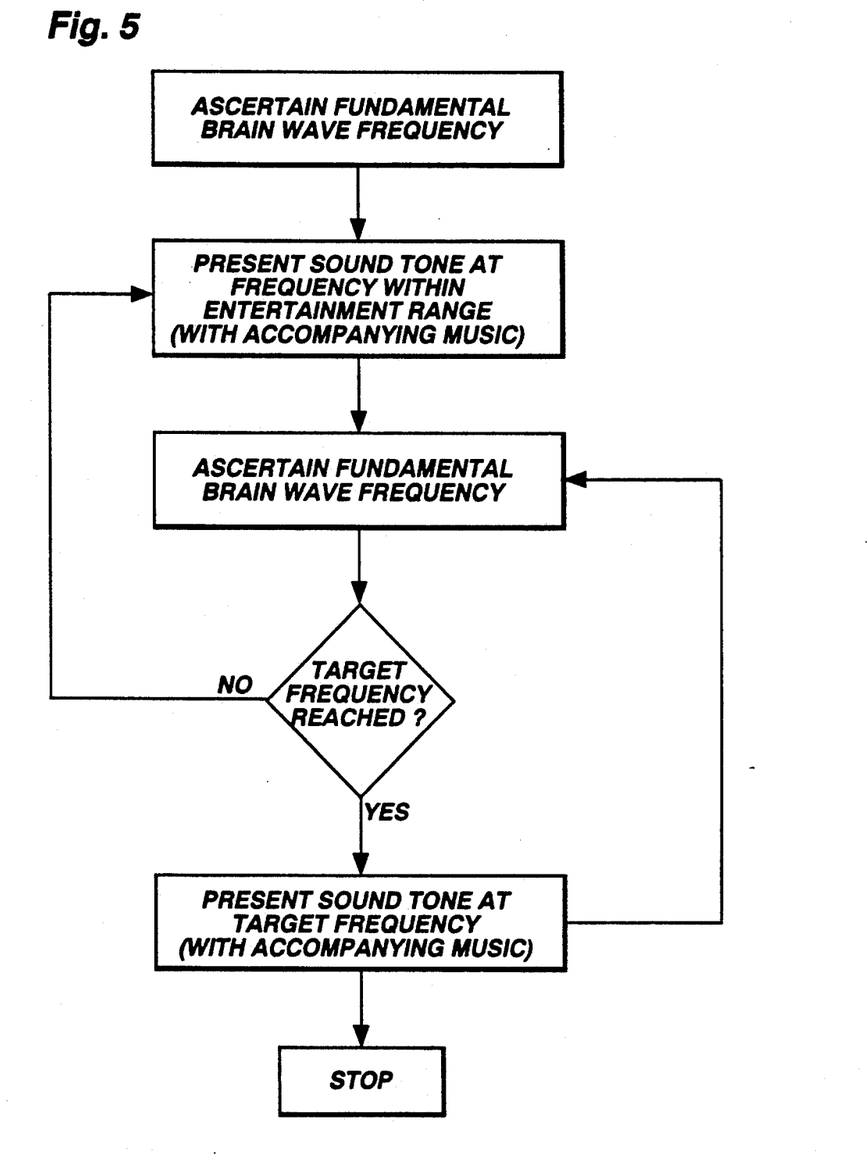
FIG. 5 is a flow chart of an example of a method of interactively entraining brain wave frequencies according to the invention.

Referring now to FIG. 5, another embodiment of the invention is shown in flow chart form. In this embodiment, the frequency of the brain waves generated by the patient are changed through interactive entrainment. First, the patient is subjected to an electroencephalograph (EEG) which detects brain wave activity and, with the help of a Fourier transform or other process known in the art, ascertains the fundamental brain wave frequency. A tone having a frequency within the entrainment range of the fundamental brain wave is then presented to the patient. The tone may be presented alone or with accompanying music; the combination is preferable for the reasons stated above.

The fundamental EEG frequency can be used for purposes of interactive entrainment, or any other frequency detected by the EEG can similarly be used, though the utility of this would likely be less than entrainment of the fundamental frequency. Brain wave frequencies fall into one of six (6) different bands, and may be interactively entrained to any other frequency band. The frequency bands are delta, 1.5–3.5 Hz, theta, 4.0–7.5 Hz, alpha, 8,0–12.5 Hz, betal, 13.0–18.0 Hz, beta2, 18.5–24.0 Hz, and beta3, 24.5–31.5 Hz.

The tone presented to the patient may comprise a low, perhaps subaudible, fundamental tone, i.e., with a frequency ranging from 5 Hz to 25 Hz, with overtones (harmonics) generated up to about 90 Hz. Harmonic tones are whole number multiples of the fundamental; therefore, a subaudible tone of 10 Hz, for example, will generate harmonic frequencies of 20, 30, 40, 50, 60, 70, 80, and 90 Hz, creating a repetition frequency of 10 Hz. A tone of 15 Hz will generate a repetition frequency of 15 Hz. The repetition frequency is set within the entrainment range of the fundamental EEG frequency to entrain the latter. After the testing time period, the fundamental EEG frequency is again ascertained and the tone (and repetition frequency) are changed as needed and again presented to coax the EEG frequency to the target frequency, similarly to the methods previously described.

Other tones besides those generating repetition frequencies may be used for interactive entrainment of brain waves, such as the beat frequency resulting from the simultaneous sounding of two pure tones that differ only minimally in their frequencies, differing approximately between 0.2 and 3.0 Hz. Low frequency pure tones, 20 to 90 Hz, are used to generate the beat frequency.

The embodiment of FIG. 5 has practical applications including stress reduction for individuals who cannot or will not benefit from biofeedback training, e.g., mentally retarded persons, the emotionally disturbed, and young children. It can also be used to increase EEG rhythms to allow certain children with learning disabilities to function more efficiently in learning situations, and to treat individuals of all ages having problems related to abnormal EEG profiles such as epilepsy.

It will be appreciated that the methods described herein are specific embodiments of the invention and that other embodiments will be apparent to those skilled in the art in light of this disclosure. The invention is not limited to the specific embodiments described.

Following is an example of a treatment study of the method of FIG. 2.

EXAMPLE

Sixty-four undergraduate students (32 males and 32 females; mean age 21.7 years) from two general education music classes and one sociology class at Utah State University served as subjects. Two hundred and twenty-four students originally volunteered to participate in the study. Each of these students completed a questionnaire designed to determine whether previous musical training or current physically related problems would preclude their participation. As musicians may respond differently from nonmusicians to musical stimuli, only nonmusicians were eligible to serve as subjects. Nonmusicians were defined as individuals who had not received formal music training and/or had not actively performed music after the eighth grade.

Ninety-eight students were deleted from the original pool due to prior musical training and three students were deleted due to physical problems (i.e., heart disease, hearing impairment, and a nervous system disorder). The remaining 123 volunteers provided the pool from which 64 subjects were randomly assigned to one of four experimental groups: tempo 1, tempo 2, physiologically interactive tempi (PIT), or music with interactive frequency in accord with FIG. 2 and a no music control. Each group comprised eight males and eight females, each group totaling 16.

The initial questionnaire was also designated to obtain information relevant to each subject's music preferences. While it was necessary to determine each subject's style preference for relaxation music, care was taken not to sensitize the subjects to the purposes of the study. Therefore, other extraneous music preference items were included on the questionnaire.

Baroque music was employed in this study. As subjects' music preferences can affect their psychological responses to music, it was necessary to have an equal number of subjects in each group whose preferred relaxation music was of a classical nature. The group assignments of 6 of the 64 subjects were adjusted to create this balance (i.e., five subjects with a classical preference in each group).

All of the subjects in the three music listening groups (i.e., tempo 1, tempo 2, PIT) listened to the same Bach Three-Part Inventions (Sinfonias) presented in the same sequence (Numbers 8, 1, 12, and 14). Each invention was repeated once before the next invention was begun. The selections were recorded using a Kawai K-1 Digital Synthesizer and an Alesis MMT-8 Multitrack MIDI Sequencer Recorder. The music was slightly altered, as an additional quarter note bass part was provided one octave beneath the original bass part in order to create a consistent pulse pattern.

The musical selections were presented to the subjects using the aforementioned synthesizer equipment amplified through a Yamaha A460 Amplifier. Subjects listened to the music through stereophonic headphones (Sennhieser, HO-450). All music was presented using the piano 2 pre-setting on the synthesizer to control timbre. The volume controls on the synthesizer and amplifier were taped in a fixed position to control the intensity of the music presentations. The intensity levels of the presentations ranged from 68 to 82 db's (Realistic Sound Level Meter No. 33-2050).

All subjects were presented nine minutes of music. The tempo 1 group listened to music at a slow consistent tempo (M.M.=48) and the tempo 2 group was presented music at a faster consistent tempo (M.M.=86). The PIT subjects were presented music at tempi approximately one beat below their ongoing heart rates which required special procedures.

The process of presenting the PIT music required an experimenter to manually manipulate tempo changes throughout each musical presentation for each subject. The ongoing tempi of the music were adjusted through the use of the Alesis MIDI Recorder (AMR). The AMR provided a digital display of the tempo in whole number beats per minute (e.g., 62, 63, etc.). In order to change the tempo, an experimenter would depress a tempo button and simultaneously depress either a plus or minus button which would rapidly increase or decrease the tempo.

The heart rate instrument (Thought Technology, HR 101 T) was positioned on the AMR so that the digital displays of heart rate (HR) and tempo were only 6.3 centimeters apart. This permitted the experimenter to monitor both digital displays simultaneously. The HR display was provided in tenths of a beat (e.g., 71.4). The experimenter adjusted the tempo in whole number increments one beat below the whole number HR reading. Therefore, while the PIT condition was described as music presented approximately one beat below ongoing HR, the difference between tempo and HR could range from 1 to 1.9 beats.

This manual process was easier to employ than was first anticipated. While normal HR activity manifests beat by beat changes which would have been difficult to follow (i.e., 62.4, 66.3, 61.2, etc.), the HR 101 T was designed to smooth out HR data by providing moment by moment (about every half-second) readings based on 3-section averages. Therefore, HR data were presented in a more linear manner (i.e., 62.3, 62.5, 62.8, 63.1, etc.). The experimenter could anticipate tempo increases and decreases by monitoring the direction of the HR changes in tenths of a beat prior to changing the tempo to one whole number beneath the HR reading.

A plethysmograph (Thought Technology, HR 101 T) was employed in measuring heart rate. A biofeedback-computer interface system (BIO-TRACK, RMX-1; Apple IIe computer) was utilized for data acquisition and computation purposes.

Sessions were conducted in a room (4.26 m×4.87 m) with white walls and no decorations. A recliner was positioned in the center of the room. The instrumentation utilized in the study (i.e., physiological instrumentation, computer, synthesizer, etc.) were positioned behind the recliner. The video camera used for reliability data was also positioned behind the recliner. Lighting in the room was moderate, as it was felt that either dim or bright lighting could influence subject responses. Some general office furnishing (i.e., file cabinets, bookshelves) were present.

Each subject participated in an individual 30-minute session. Upon arrival, the subject was seated in the recliner in an upright position and was presented with a copy of the informed consent form. The consent form was carefully worded so that the procedures were clearly delineated without sensitizing the subject to the specific purposes of the investigation. The subject was informed that certain of his or her physiological responses were being measured while they listened to music. Each subject agreed to wait until the conclusion of the entire study before being informed of the specific physiological measures which were monitored. This procedure was considered necessary to ensure that subjects who had completed their sessions would not share this information with other subjects prior to their sessions.

Each subject was informed that the music preference information that they had provided on the initial questionnaire would be useful to the experimenter, but did not have a bearing on the music that they were to be presented. The subject was informed that all subjects, with the exception of the control group subjects, would listen to the same musical selections.

Upon completion of the informed consent procedures the subject was placed in a reclining position. The HR receptor was attached to the subject's index finger (right hand) by slipping an elastic band around the finger. The subject's arms were placed comfortably on the arm rests of the recliner. The EMG electrode receptors were then attached to the subject's forehead (frontalis muscle) using Spectra 360 electrode gel. The procedures utilized for attaching the EMG electrodes and testing the quality of the electrode placements (impedance testing) were those detailed in the Instruction Manual for the Autogen 1100 (*Autogenic Systems*, Inc., 1975). The stereophonic headphones were then placed on the subject. Subjects in the no music control group also wore headphones.

The subject was asked to close his or her eyes and find a comfortable position. Once comfortable, the subject was asked to remain still and simply listen to the music when it was presented in another 6 minutes.

At this point of the session the subject had already been sitting in a reclining position for at least 5 minutes. Another 3-minute period of silence was now provided to ensure that the subject would achieve a resting HR prior to the acquisition of baseline data.

Physiological data (i.e., HR & EMG) were recorded during a 3-minute baseline period and three subsequent 3-minute periods comprising the nine-minute treatment condition for each subject. The BIO-TRACK computer program calculated means for each dependent variable for each of the four 3-minute periods (i.e., baseline and the three 3-minute treatment periods).

Immediately following the 3-minute baseline period subjects in the tempo 1, tempo 2, and PIT groups were presented the appropriate nine minutes of music. Subjects in the control group sat in silence. One experimenter was present to monitor the session and to present the PIT music to subjects in that group.

Correlated t tests were performed comparing baseline means with means from each of the three 3-minute periods comprising the 9-minute treatment conditions. This provided information relevant to the amount of HR change that occurred over time.

Data in Table 1 indicates that no significant differences in HR occurred during Period 1. However, the PIT group evidenced the greatest HR change, yielding the only t value to approach a level of significance ($p=0.061$). During Periods 2 and 3 (see Table 1) significant HR decreases were demonstrated by the PIT group ($p<0.001$) and the control group ($p<0.05$) with the greatest decreases occurring in the PIT group. The HR's of the tempo 1 (slower tempo) group decreased minimally and nonsignificantly while the HR's of the tempo 2 (faster tempo) group increased minimally and nonsignificantly during Periods 2 and 3.

TABLE I

| Group | Mean Comparisons for Heart Rate | | | |
|---|---|---|---|---|
| | Baseline | Period 1 | Period 2 | Period 3 |
| No Music | | | | |
| M | 64.2750 | 64.0500 | 63.1688 | 62.6688 |
| SD | 7.445 | 7.786 | 7.579 | 6.702 |
| t | — | .43 | 2.38* | 2.17* |
| Tempo 1 | | | | |
| M | 67.7062 | 67.8687 | 67.6563 | 67.1375 |
| SD | 9.550 | 9.155 | 9.186 | 8.930 |
| t | — | .49 | .10 | .87 |
| Tempo 2 | | | | |
| M | 61.5625 | 61.7313 | 61.8000 | 61.7125 |
| SD | 7.777 | 7.795 | 7.809 | 7.572 |
| t | — | −.55 | −.75 | −.35 |
| PIT | | | | |
| M | 65.2750 | 64.3688 | 63.7063 | 63.1500 |
| SD | 10.895 | 11.320 | 11.000 | 10.536 |

TABLE I-continued

| Group | Mean Comparisons for Heart Rate | | | |
|---|---|---|---|---|
| | Baseline | Period 1 | Period 2 | Period 3 |
| t | — | 2.03 | 4.40** | 3.89** |

*$p < .05$
**$p < .001$

Treatment effects were analyzed for each of the three periods by performing a separate one-way analysis of variance (ANOVA) on the change of HR from baseline for each period. No significant treatment effects were observed in the ANOVA performed on Period 1 data ($F=1.5125$; $df=3, 60$; $p=0.2205$). An ANOVA examining Period 2 data revealed significant treatment effects ($F=4.0770$; $df=3, 60$; $p=0.0106$). Fisher's LSD test was utilized as a follow-up procedure to determine where significant between-group differences occurred. The LSD test determines whether groups are significantly different at the 0.05 level. Fisher's LSD test confirmed that the HR decreases demonstrated by the PIT group were significantly different ($p<0.05$) from the HR responses of subjects from both the tempo 1 and tempo 2 groups during Period 2. The HR responses of the control group were significantly different ($p<0.05$) from those of the tempo 2 (faster tempo) group.

Significant treatment effects were also observed in the ANOVA performed on Period 3 data ($F=2.8650$; $df=3, 60$; $p=0.0440$). Fisher's LSD test demonstrated that HR data for the PIT group and the control group were each significantly different ($p<0.05$) from the tempo 2 group's data but not from the tempo 1 group's data.

Figure 6:
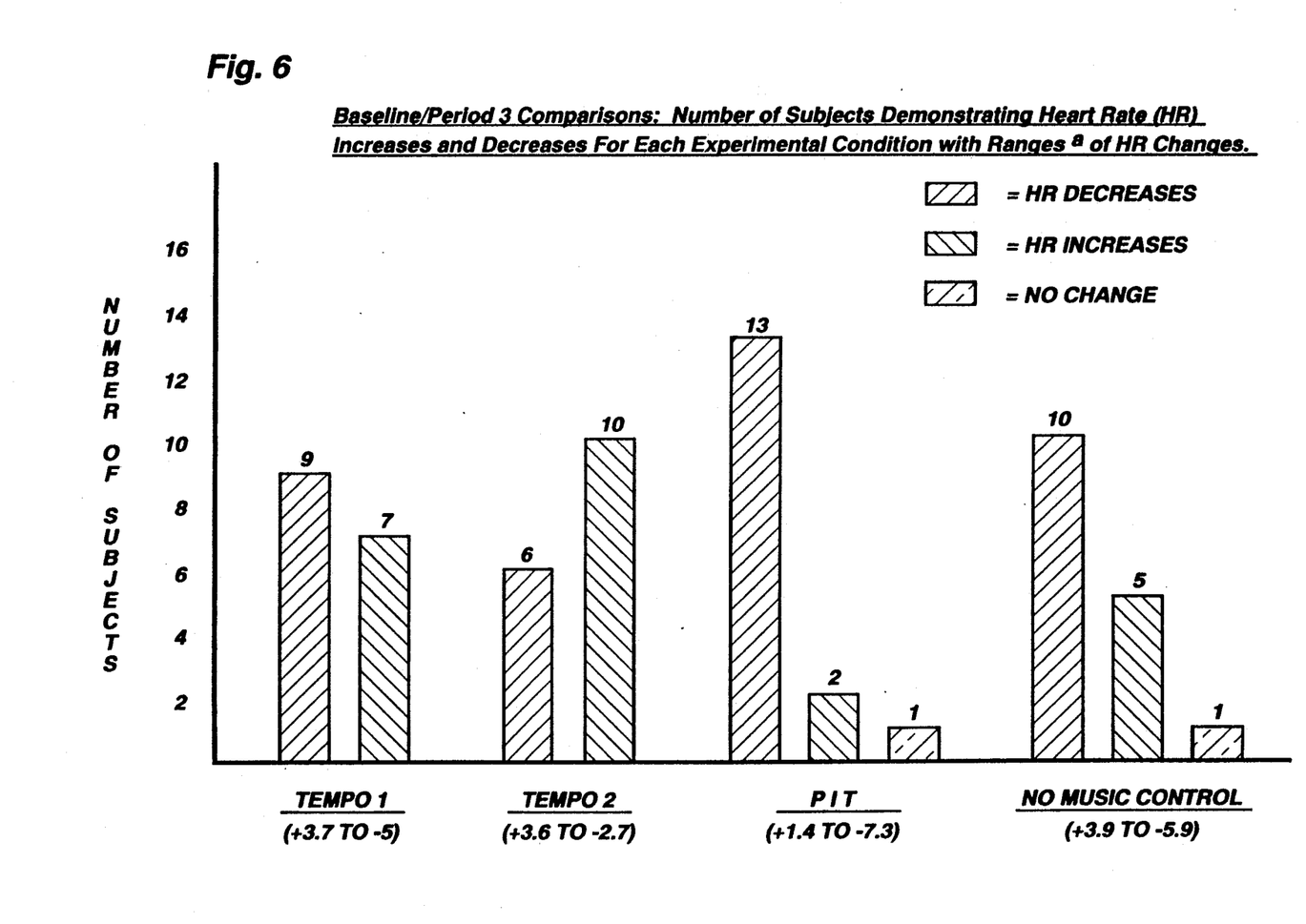
FIG. 6 is a bar graph chart of a comparison of heart rate increases and decreases from a treatment study using the method of FIG. 2.

Descriptive data presented in the graph of FIG. 6 provides information regarding the number of subjects in each experimental group that demonstrated HR increases and decreases, as well as the range of HR changes demonstrated within each group. These data indicate that the PIT condition was the most effective in eliciting HR decreases. Range data demonstrates that the greatest HR increase for the PIT group was also notably below the greatest decreases demonstrated by subjects in the other groups.

What is claimed is:

1. A method of interactively influencing a patient's physiological process having a frequency, in order to change the frequency of the process to a target frequency, comprising the steps of:
    ascertaining the frequency of the physiological process at a first point in time;
    exposing the patient to rhythmic sound stimuli having a frequency within a predetermined entrainment range of the physiological process frequency;
    ascertaining the frequency of the physiological process at a second point in time;
    determining any change in frequency of the physiological process between the first point and second point in time;
    adjusting the frequency of the rhythmic sound stimuli in response to the change of the physiological process frequency to bring the frequency of the rhythmic sound stimuli within the predetermined entrainment range;
    exposing the patient to the rhythmic sound stimuli having its adjusted frequency.

2. The method of claim 1 wherein the rhythmic sound stimuli comprises music.

3. The method of claim 1 further comprising the step of exposing the patient to tactile stimuli at a frequency approximately equal to the frequency of the rhythmic sound stimuli.

4. The method of claim 1 wherein the physiological process frequency is the heart rate of the patient.

5. The method of claim 4 wherein the step of exposing the patient to rhythmic sound stimuli includes exposing the patient to music which has a tempo of a frequency within the predetermined entrainment range.

6. The method of claim 4 wherein the step of exposing the patient to rhythmic sound stimuli having a frequency within a predetermined entrainment range includes exposing the patient to music having a tempo which differs from the heart rate between 1 and 0.01 beats per minute.

7. The method of claim 1 further comprising the steps of ascertaining the frequency of the physiological process at a third point in time, determining the change in frequency of the physiological process between the second point and third point in time, adjusting the frequency of the sound stimuli in response to the change in frequency of the physiological process to bring the frequency of the sound stimuli within the predetermined entrainment range, and exposing the patient to the sound stimuli with its adjusted frequency.

8. The method of claim 1 wherein the step of exposing the patient to rhythmic sound stimuli includes exposing the subject to pre-programmed synthesizer music at a predetermined tempo.

9. The method of claim 8 further comprising the step of exposing the patient to tones having a frequency between approximately 20 and 30 Hz as the bass portion of the music.

10. The method of claim 1 wherein the physiological process is the patient's fundamental brain wave frequency.

11. The method of claim 1 wherein the physiological process is the respiration rate of the patient.

12. A method of interactively entraining a physiological process having a determinable frequency in a patient toward a target frequency comprising the steps of:
  making a first determination of the frequency of the physiological process;
  presenting sound stimuli to the patient during a predetermined first time interval, the sound stimuli having a frequency within a predetermined entrainment range of the frequency of the physiological process;
  making a second determination of the frequency of the physiological process, thereby determining the direction of and extent to which the physiological process frequency has varied from the time of the first determination;
  changing the frequency of the sound stimuli to approximately the same extent and in the same direction as the change in frequency of the physiological process;
  presenting the sound stimuli to the patient during a predetermined second time interval.

13. The method of claim 12 further comprising the step of repeating the steps of the method until the frequency of the physiological process is approximately the same as the target frequency.

14. The method of claim 13 further comprising the step of making the frequency of the sound stimuli approximately the same as the target frequency.

15. The method of claim 14 further comprising the step of monitoring the frequency of the physiological process and changing the frequency of the sound stimuli to remain within the entrainment range of the physiological process frequency if the latter substantially deviates from the target frequency.

16. The method of claim 12 wherein the physiological process is the heartbeat of the patient, the frequency of the physiological process is the heart rate, the sound stimuli is music, and the frequency of the sound stimuli is the tempo of the music.

17. The method of claim 12 wherein the physiological process is the brain wave activity of the patient, the frequency of the physiological process is the frequency of a predetermined frequency component of the brain wave activity, the sound stimuli is a continuous tone, and the frequency of the sound stimuli is the frequency in Hertz units of the continuous tone.

18. The method of claim 17 wherein the predetermined frequency component of the brain wave activity is the fundamental frequency of the brain wave.

19. The method of claim 17 further comprising the step of presenting music to the patient in conjunction with the continuous tone.

20. The method of claim 12 wherein the physiological process is the brain wave activity of the patient, the frequency of the physiological process is the frequency of a predetermined frequency component of the brain wave activity, the sound stimuli is a continuous fundamental tone together with harmonic overtones comprising whole number multiples of the fundamental tone thereby generating a repetition frequency, and the frequency of the sound stimuli is the repetition frequency.

21. The method of claim 12 wherein the physiological process is the brain wave activity of the patient, the frequency of the physiological process is the frequency of a predetermined frequency component of the brain wave activity, and the frequency of the sound stimuli is the beat frequency resulting from the simultaneous sounding of two pure tones that differ only minimally in their frequencies.

22. The method of claim 12 wherein the physiological process is the respiration of the patient, the frequency of the physiological process is the respiration rate of the patient, the sound stimuli is music, and the frequency of the sound stimuli is the tempo of the music.

23. A method of varying the heart rate of a person, the heart rate having a frequency, from a first heart rate frequency to a second heart rate frequency comprising the steps of:
  (1) exposing the person to music having a tempo within an entrainment range of the first heart rate frequency;
  (2) ascertaining the change, if any, in the person's heart rate frequency;
  (3) determining whether the music tempo is still within an entrainment range of the heart rate frequency and if so, changing the tempo to fall once again within an entrainment range of the heart rate frequency;
  (4) exposing the person to the music with the changed tempo;
  (5) repeating steps (1) through (4) until the heart rate frequency reaches the second heart rate frequency.

24. The method of claim 23 further comprising the step of exposing the person to low frequency tones corresponding to the bass part of the music.

25. The method of claim 23 further comprising the step of exposing the person to tactile stimulation corresponding to the tempo of the music.

26. The method of claim 23 wherein the entrainment range is 0.19 beats per minute.

27. The method of claim 23 wherein the tempo of the music differs from the heart rate by a maximum of 0.19 beats per minute.

28. A method of changing a component brain wave frequency of a person from a first frequency to a target frequency comprising the steps of:
   (1) determining the first frequency of the component frequency at a first point in time;
   (2) subjecting the person to a first sound tone having a frequency near the first frequency;
   (3) determining the frequency of the component frequency at a second point in time;
   (4) subjecting the person to a second sound tone in place of the first sound tone, the second sound tone having a frequency near the frequency of the component frequency as determined at the second point in time;
   (5) repeating steps (1) through (4) until the component frequency approximates the target frequency;
   wherein the sound tones are continuous fundamental tones, together with harmonic overtones comprising whole number multiples of the fundamental tones, thereby generating a repetition frequency, and wherein the frequencies of the sound tones are the repetition frequencies.

29. The method of claim 28 wherein the component frequency is the fundamental brain wave frequency.

30. The method of claim 28 wherein the first and second sound tones each have a frequency within the entrainment range of the component frequency.

31. The method of claim 28 further comprising the step of subjecting the person to music in combination with the sound tones.

32. The method of claim 28 wherein the sound tones each comprise the beat frequency resulting from the simultaneous sounding of two pure tones that differ only minimally in their frequencies.

33. The method of claim 32 wherein the two pure tones differ approximately between 0.2 and 3.0 Hz.

34. The method of claim 32 wherein the two pure tones each have frequencies of between approximately 20 to 90 Hz.

* * * * *